United States Patent
Aghassian

(10) Patent No.: US 10,105,545 B2
(45) Date of Patent: Oct. 23, 2018

(54) ASSEMBLY WITH A COAXIAL AUDIO CONNECTOR FOR CHARGING AN IMPLANTABLE MEDICAL DEVICE

(71) Applicant: Boston Scientific Neuromodulation Corporation, Valencia, CA (US)

(72) Inventor: Daniel Aghassian, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 272 days.

(21) Appl. No.: 15/050,028

(22) Filed: Feb. 22, 2016

(65) Prior Publication Data

US 2016/0263385 A1 Sep. 15, 2016

Related U.S. Application Data

(60) Provisional application No. 62/131,975, filed on Mar. 12, 2015.

(51) Int. Cl.
*A61N 1/00* (2006.01)
*A61N 1/378* (2006.01)
(Continued)

(52) U.S. Cl.
CPC .......... *A61N 1/3787* (2013.01); *H02J 7/025* (2013.01); *H02J 50/10* (2016.02); *H04B 5/0037* (2013.01);
(Continued)

(58) Field of Classification Search
CPC ........ A61N 1/3787; H02J 50/10; H02J 7/025; H02J 50/80; H02J 50/90; H02J 7/0054; H04B 5/0037; H04B 5/0081
See application file for complete search history.

(56) References Cited

U.S. PATENT DOCUMENTS

| 4,561,443 A | 12/1985 | Hogrefe et al. |
| 5,314,457 A | 5/1994 | Jeutter |

(Continued)

FOREIGN PATENT DOCUMENTS

| JP | 2004-73725 | 3/2004 |
| WO | 2005/032658 | 4/2005 |

(Continued)

OTHER PUBLICATIONS

International Search Report and Written Opinion regarding corresponding PCT Application No. PCT/US2016/019031, dated May 4, 2016.

(Continued)

*Primary Examiner* — Lindsey G Wehrheim
(74) *Attorney, Agent, or Firm* — Lewis & Reese, PLLC

(57) ABSTRACT

Disclosed is a charging coil assembly for a mobile device able to wirelessly provide power to charge a battery in an Implantable Medical Device (IMD). The assembly includes a coaxial connector that can be inserted into a coaxial audio port on the mobile device to allow bi-directional communications between the assembly and the mobile device. One or more housings coupled to the connector by a cable can include control circuitry, a charging coil, and a battery. The charging coil can be driven by control circuitry in the assembly or by a charging audio signal at an audio frequency provided by the mobile device via the audio port and connector. A Charging Application on the mobile device can detect and authenticate the charging coil assembly, and render a charging graphical user interface on the mobile device to control and/or monitor charging of the IMD.

25 Claims, 7 Drawing Sheets

(51) Int. Cl.
*H02J 7/02* (2016.01)
*H02J 50/10* (2016.01)
*H04B 5/00* (2006.01)
*H02J 7/00* (2006.01)
*H02J 50/90* (2016.01)
*H02J 50/80* (2016.01)

(52) U.S. Cl.
CPC .......... *H04B 5/0081* (2013.01); *H02J 7/0054* (2013.01); *H02J 50/80* (2016.02); *H02J 50/90* (2016.02)

(56) References Cited

U.S. PATENT DOCUMENTS

| | | |
|---|---|---|
| 6,505,077 B1 | 1/2003 | Kast |
| 6,516,227 B1 | 2/2003 | Meadows |
| 6,553,263 B1 | 4/2003 | Meadows |
| 6,658,300 B2 | 12/2003 | Govari |
| 7,177,698 B2 | 2/2007 | Klosterman et al. |
| 7,200,504 B1 | 4/2007 | Fister |
| 7,286,880 B2 | 10/2007 | Olson et al. |
| 7,428,438 B2 | 9/2008 | Parramon et al. |
| 8,335,569 B2 | 12/2012 | Aghassian |
| 8,463,392 B2 | 6/2013 | Aghassian |
| 8,498,716 B2 | 7/2013 | Chen et al. |
| 8,588,925 B2 | 11/2013 | Carbunaru et al. |
| 8,682,444 B2 | 3/2014 | Aghassian et al. |
| 8,744,098 B2* | 6/2014 | Rothkopf ............ H02J 7/00 320/108 |
| 9,186,518 B2 | 11/2015 | Kothandaraman |
| 2003/0078634 A1 | 4/2003 | Schulman et al. |
| 2004/0098068 A1 | 5/2004 | Carbunaru et al. |
| 2005/0021108 A1 | 1/2005 | Klosterman et al. |
| 2005/0088357 A1 | 4/2005 | Hess et al. |
| 2005/0113887 A1 | 5/2005 | Bauhahn |
| 2005/0143781 A1 | 6/2005 | Carbunaru et al. |
| 2005/0187590 A1 | 8/2005 | Boveja et al. |
| 2007/0060967 A1 | 3/2007 | Strother et al. |
| 2007/0060980 A1 | 3/2007 | Strother et al. |
| 2007/0270921 A1 | 11/2007 | Strother et al. |
| 2008/0027513 A1 | 1/2008 | Carbunaru |
| 2009/0069869 A1 | 3/2009 | Stouffer et al. |
| 2009/0112291 A1 | 4/2009 | Wahlstrand et al. |
| 2009/0118796 A1 | 5/2009 | Chen et al. |
| 2010/0204756 A1 | 8/2010 | Aghassian |
| 2012/0012630 A1 | 1/2012 | Lui et al. |
| 2012/0101551 A1 | 4/2012 | Aghassian et al. |
| 2013/0096651 A1 | 4/2013 | Ozawa et al. |
| 2013/0123881 A1 | 5/2013 | Aghassian |
| 2013/0253612 A1 | 9/2013 | Chow |
| 2014/0025140 A1 | 1/2014 | Lui et al. |
| 2014/0114373 A1 | 4/2014 | Aghassian |
| 2014/0324126 A1 | 10/2014 | Ozawa |
| 2014/0358194 A1 | 12/2014 | Vansickle et al. |
| 2015/0100108 A1 | 4/2015 | Vansickle et al. |
| 2015/0100109 A1 | 4/2015 | Feldman et al. |
| 2015/0231402 A1 | 8/2015 | Aghassian |
| 2015/0360038 A1 | 12/2015 | Zottola et al. |

FOREIGN PATENT DOCUMENTS

| | | |
|---|---|---|
| WO | 2007/124325 | 11/2007 |
| WO | 2014/137319 A1 | 9/2014 |

OTHER PUBLICATIONS

U.S. Appl. No. 14/826,050, filed Aug. 2015, Aghassian.
U.S. Appl. No. 14/789,564, filed Jul. 2015, Ter-Petrosyant et al.
Medtronic, Inc.'s Restore™ Rechargeable Neurostimulation System, as described in Applicant's Information Disclosure Statement filed herewith.
Advanced Neuromodulation Systems (ANS), Inc. Eon™ Neurostimulation Systems IPG, as described in Applicant's Information Disclosure Statement filed herewith.

* cited by examiner

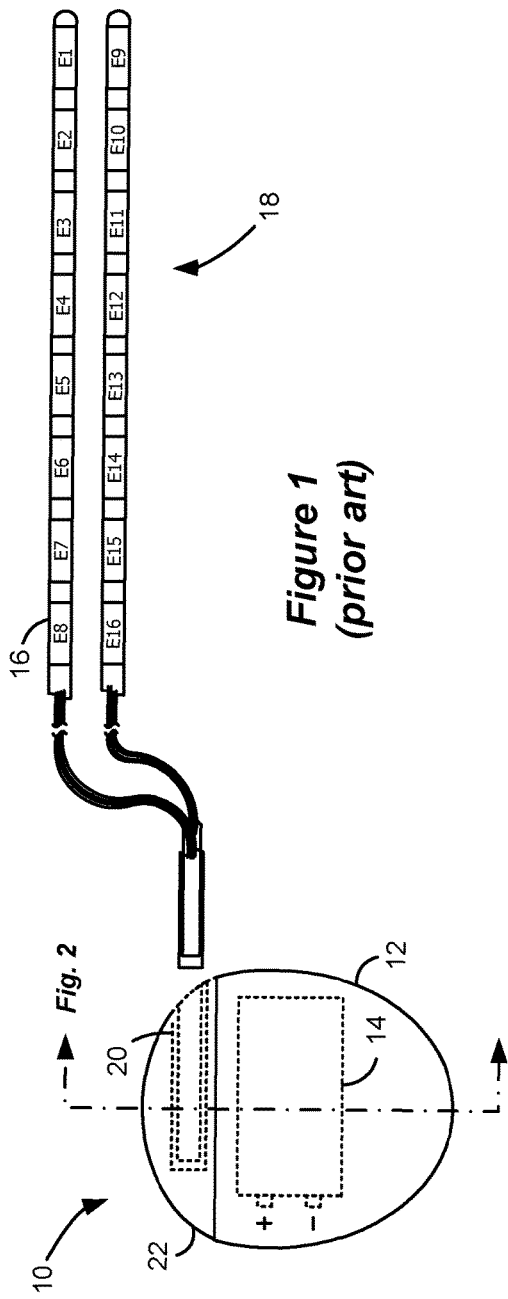
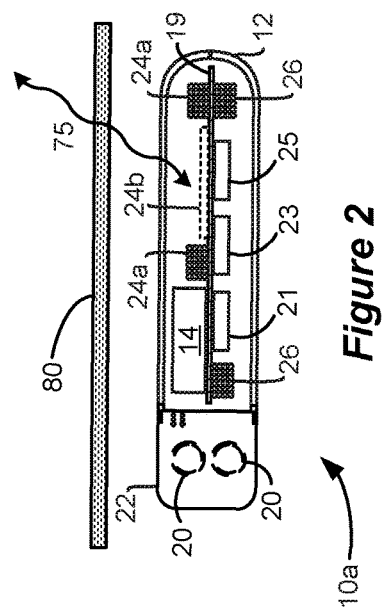
Figure 1 (prior art)
Figure 2 (prior art)

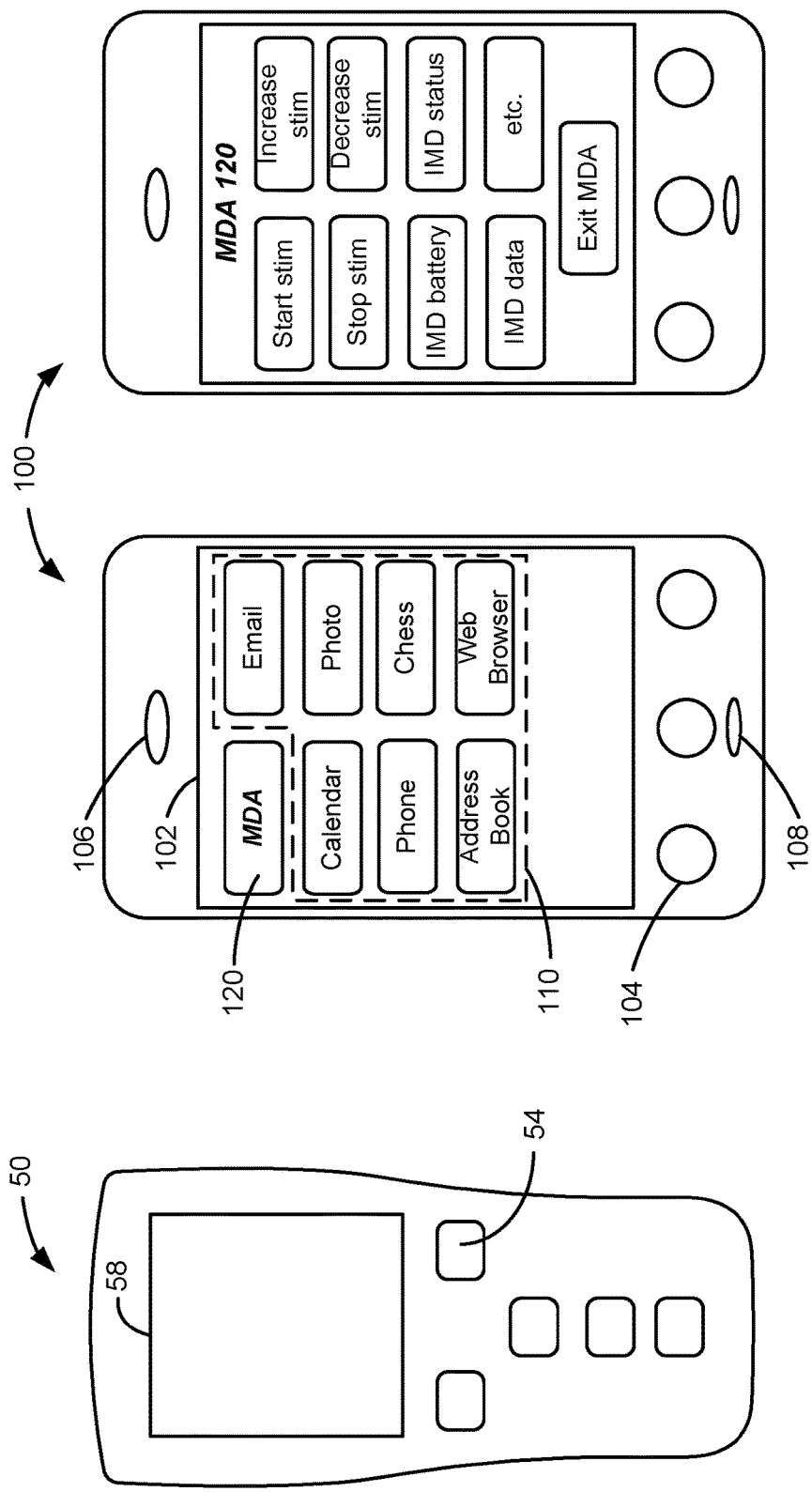

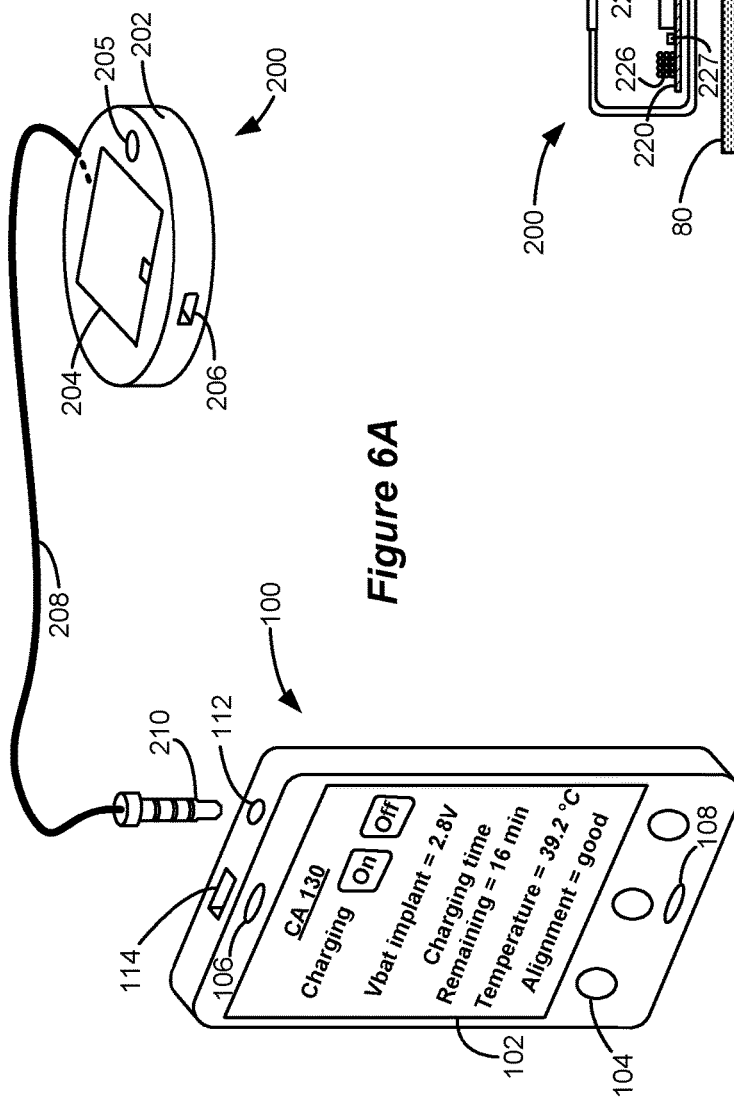
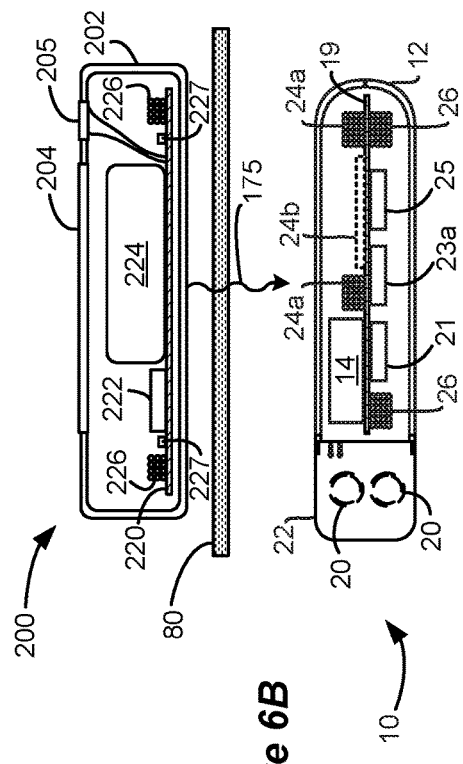
Figure 6A
Figure 6B

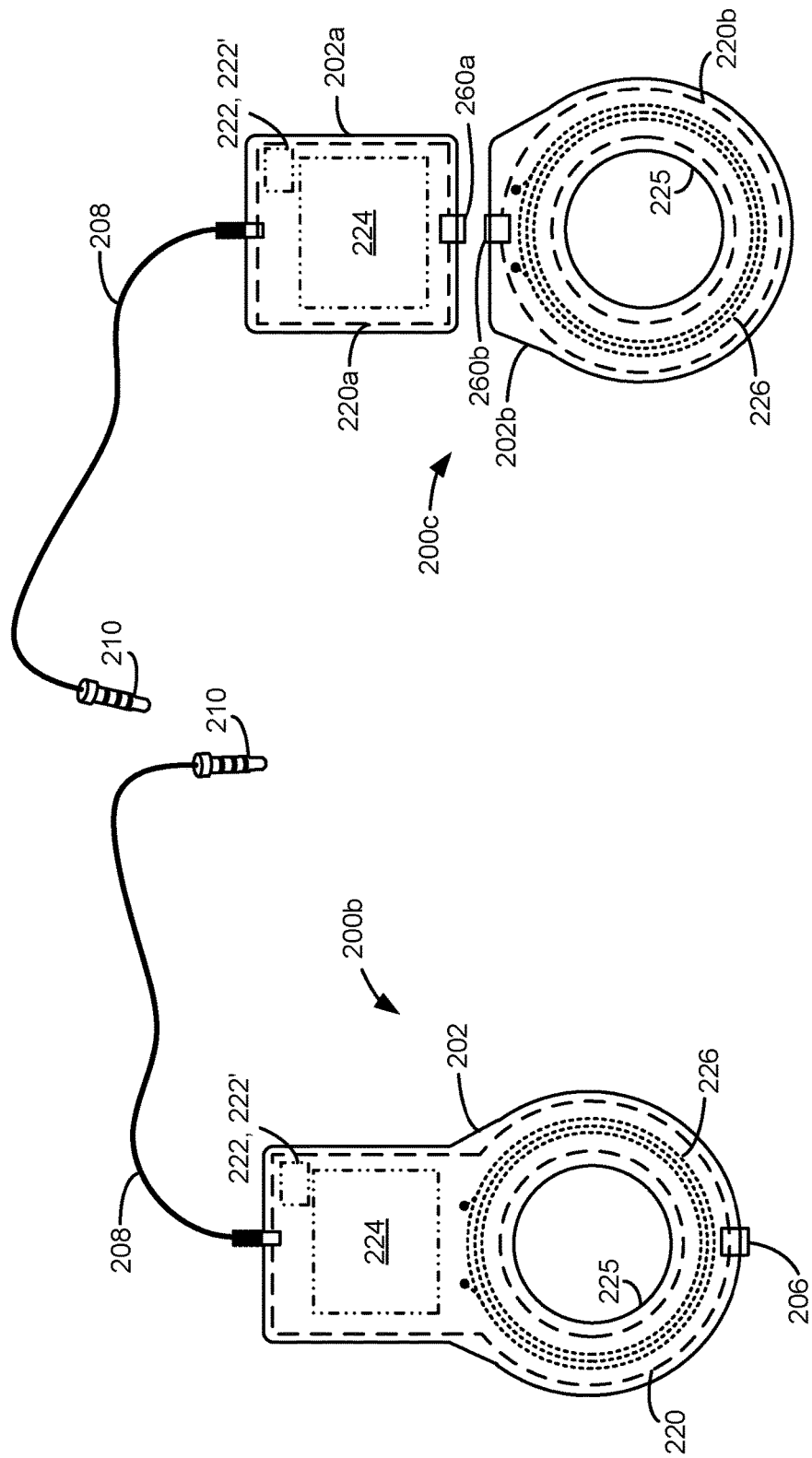

ASSEMBLY WITH A COAXIAL AUDIO CONNECTOR FOR CHARGING AN IMPLANTABLE MEDICAL DEVICE

CROSS REFERENCE TO RELATED APPLICATIONS

This is a non-provisional of U.S. Provisional Patent Application Ser. No. 62/131,975, filed Mar. 12, 2015, to which priority is claimed, and which is incorporated by reference in its entirety.

FIELD OF THE INVENTION

The present invention relates generally to implantable medical device systems, and more particularly to an assembly useable with a mobile external device to facilitate charging of an implantable medical device.

BACKGROUND

Implantable stimulation devices deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators (DBS) to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any implantable medical device (IMD) or in any implantable medical device system.

As shown in FIG. 1, a SCS system includes an implantable pulse generator 10 (hereinafter, and more generically, IMD 10), which includes a biocompatible device case 12 formed of titanium for example. The case 12 typically holds the circuitry and battery 14 necessary for the IMD 10 to function. The IMD 10 is coupled to electrodes 16 via one or more electrode leads 18 (two of which are shown). The proximal ends of the leads 18 are coupled to the IMD 10 at one or more lead connectors 20 fixed in a header 22, which can comprise an epoxy for example. In the illustrated embodiment, there are sixteen electrodes, although the number of leads and electrodes is application specific and therefore can vary. In an SCS application, two electrode leads 18 are typically implanted on the right and left side of the dura within the patient's spinal column. The proximal ends of the leads 18 are then tunneled through the patient's flesh to a distant location, such as the buttocks, where the IMD case 12 is implanted, at which point they are coupled to the lead connectors 20.

A cross section of IMD 10 is shown in FIG. 2. A telemetry antenna 24a or 24b is used to transcutaneously communicate data through the patient's tissue 80 with devices external to the patient via wireless link 75, such as the external controller 50 of FIG. 3 and/or the mobile device 100 of FIGS. 4A and 4B, as will be explained subsequently. Telemetry antenna 24a comprises a coil for providing near-field magnetic induction communications along link 75, whereas telemetry antenna 24b comprises a patch, slot, or wire antenna for providing far-field, short-range RF communications along link 75. Either or both of antennas 24a and 24b can be provided and used in IMD 10, and may also be placed within the IMD's header 22, or on the outside of the case 12 as explained in U.S. Patent Application Publication 2015/0231402, which is incorporated herein by reference.

IMD 10 further includes a charging coil 26 for wirelessly charging the IMD's battery 14 using an external charging device 150 such as that depicted in FIG. 5A, explained subsequently. IMD 10 also contains control circuitry such as a microcontroller 21, telemetry circuitry 23 for interfacing with the antenna 24a or 24b, and various components 25 necessary for IMD operation, such as stimulation circuitry for forming therapeutic pulses at the electrodes 16. The charging coil 26, battery 14, microcontroller 21, telemetry circuitry 23, and other components 25 are electrically coupled to a printed circuit board (PCB) 19.

FIGS. 3, 4A and 4B show different configurations for external devices used to communicate with IMD 10 in the prior art. Such external devices are typically used to send or adjust the therapy settings the IMD 10 will provide to the patient (such as which electrodes 16 are active to issue pulses; whether such electrodes sink or source current (i.e., polarity); the duration, frequency, and amplitude of pulses, etc.), which settings together comprise a stimulation program for the patient. External devices can also act as receivers of data from the IMD 10, such as various data reporting on the IMD's status and the level of the IMD's battery 14.

An external device having such functionality is shown in FIG. 3 in the form of a patient remote control (external controller) 50. External controller 50 is typically hand-held, portable, and powered by a battery. The external controller 50 includes a user interface similar to that used for a cell phone, including buttons 54 and a display 58, and may have other interface aspects as well, such as a speaker. Although not shown, the external controller 50 would also include within its housing communication means (including a coil antenna or a short-range RF antenna) compatible with the link 75 and the communication means in the IMD 10.

External devices such as the external controller 50 of FIG. 3 were historically built by manufacturers of IMDs, and thus were generally dedicated to communicate only with such IMDs. However, there are many commercial mobile devices, such as cell phones, that have user interfaces and built-in communication means suitable for functioning as a wireless external controller for an IMD. Using such mobile devices as external controllers for IMDs would benefit both manufacturers and patients: manufacturers would not need to design, build, and test dedicated external controllers, and patients could control and communicate with their IMDs without the inconvenience of having to carry and purchase additional dedicated external controllers.

FIGS. 4A and 4B show an example of a mobile device 100 configured for use as an external controller for an IMD. The mobile device 100 may be a commercial, multipurpose, consumer device, such as a cell phone, tablet, personal data assistant, laptop or notebook computer, or like device—essentially any mobile, hand-holdable device capable of functioning as a wireless external controller for an IMD. Examples include the Apple iPhone or iPad, Microsoft Surface, Nokia Lumia devices, Samsung Galaxy devices, and Google Android devices for example.

As shown in FIG. 4A, the mobile device 100 includes a user interface with a display 102, which may also receive input if it is a touch screen. The mobile device 100 may also have buttons 104 (e.g., a keyboard) for receiving input from the patient, a speaker 106, and a microphone 108. Shown on the display 102 is a typical home screen graphical user interface provided by the mobile device 100 when first booted or reset. A number of applications ("apps") 110 may be present and displayed as icons on the mobile device home screen, which the patient can select and execute.

One of the applications (icons) displayed in FIG. 4A is a Medical Device Application (MDA) 120, which when executed by the patient will configure the mobile device 100 for use as an external controller to communicate with an IMD. FIG. 4B shows the home screen of the MDA 120 after it is executed, which includes options selectable by a patient to control his stimulation program or monitor his IMD. For example, the MDA 120 may present options to: start or stop stimulation; increase or decrease the amplitude of the stimulation pulses (or adjust other pulse parameters and electrode settings); check the battery and operating status of the IMD; review data telemetered from the IMD; exit the MDA 120 and return to the mobile device's home screen (FIG. 4A), etc. The MDA 120, like other applications 110 selectable in the mobile device 100, may have been downloaded using traditional techniques, such as from an Internet server or an "app store."

When the MDA 120 is first selected and executed, or when an appropriate selection is made in the MDA (FIG. 4B), wireless communications with the IMD can be established using a communication means in the mobile device 100 and enabled by the MDA 120, as described in various fashions in the above-incorporated '402 Publication.

FIG. 5A shows a cross section of an external charger 150 for providing power to recharge the IMD's battery 14, and relevant circuitry in both the charger 150 and the IMD 10 is shown in FIG. 5B. The external charger 150 includes at least one PCB 152 (two are shown; see U.S. Patent Application Publication 2008/0027500); electronic components 154 some of which are subsequently discussed in FIG. 5B; a charging coil 156; and a battery 158 for providing operational power for the external charger 150 and for the production of a magnetic charging field 175 from the coil 156. These components are typically housed within a case 160, which may be made of plastic for example.

The external charger 150 has a simple user interface, which typically comprises an on/off switch 164 to activate the production of the magnetic charging field 175; an LED 166 to indicate the status of the on/off switch 164; and a speaker 168. The speaker 168 emits a "beep" for example if the external charger 150 detects via well-known alignment circuitry (not shown) that its charging coil 156 is not in good alignment with the charging coil 26 in the IMD 10 during a charging session. The external charger 150 is sized to be hand held and portable, and may be placed in a pouch around a patient's waist to position the external charger 150 in alignment with the IMD 10 during a charging session. Typically, the external charger 150 is touching the patient's tissue 80 during a charging session as shown, although the patient's clothing or the material of the pouch may intervene.

Wireless power transfer from the external charger 150 to the IMD 10 occurs transcutaneously by magnetic inductive coupling between coils 156 and 26, as illustrated in the circuitry of FIG. 5B. When the external charger 150 is activated (e.g., on/off switch 164 is pressed), a charging circuit 172 (e.g., an amplifier) under control of control circuitry 170 (e.g., a microcontroller) energizes coil 156 with a non-data-modulated AC current (Icharge) to create the magnetic charging field 175. The frequency of the magnetic charging field may be on the order of 80 kHz for example, and may be set by the inductance of the coil 156 and the capacitance of a tuning capacitor C, as is well known. The magnetic charging field 156 induces a current in the IPG 10's charging coil 26, which is generally tuned to resonate at the magnetic charging field frequency via the inductance of the charging coil 26 and its associated capacitor. The induced current is rectified 44 to DC levels and used to provide a charging current (Ibat) to recharge the IPG's battery 14, perhaps under the control of charging and battery protection circuitry 46 as shown.

The IMD 10 can also communicate data back to the external charger 150 using Load Shift Keying (LSK) telemetry. Relevant data, such as the capacity of the battery, is sent from control circuitry 21 in the IMD 10 to a LSK modulator 40, which creates a series of digital data bits. This data is input to the gate of a load transistor 42 to modulate the impedance of the charging coil 26 in the IPG 10. Such modulation of the charging coil 26 is detectable at the external charger 150 due to the mutual inductance between the coils 156 and 26, and will change the magnitude of the AC voltage needed at coil 156 (Vcoil) to drive the charging current, Icharge. LSK demodulator 174 in the external charger 70 can detect these changes in Vcoil to recover the series of digital data bits, which data is then received at control circuitry 170 so that appropriate action can be taken, such as ceasing production of the magnetic charging field 175 (i.e., setting Icharge to zero) because the battery 14 in the IMD 10 is full. See, e.g., U.S. Patent Application Publication 2013/0123881 for further details regarding the use of LSK telemetry in an external charger system.

As discussed in the above-incorporated '402 Publication, using a mobile device 100 (FIGS. 4A and 4B) to communicate with an IMD 10 is beneficial, because a patient need not additionally carry a dedicated external controller 50 (FIG. 3). However, the problem of requiring a patient to additionally carry the external charger 150 still exists.

The art however has sought to obviate the need to carry a fully-functional external charger such as that illustrated in FIG. 5A by providing a charging coil assembly that is coupleable to either or both of a dedicated external controller 50 (FIG. 3) or a mobile device 100 (FIGS. 4A & 4B). See, e.g., U.S. Pat. No. 8,498,716; U.S. patent application Ser. No. 14/826,050, filed Aug. 13, 2015. The charging coil assembly may be relatively small and easy to carry, and need not contain its own user interface as it can leverage the advanced user interfaces provided by the mobile device 100 or dedicated external controller 50 to which it is coupled. Moreover, when such a charging coil assembly is used with a mobile device, a patient may potentially only need to carry the charging coil assembly in addition to the mobile device she would already typically carry, thus providing the ability to communicate data with her IMD as well as to charge her IMD's battery 14.

Nonetheless, it cannot be guaranteed that the mobile device 100 or external controller 50 will have a port that is suitable to receive the charging coil assembly's connector. For example, the above-cited references disclose that a connector of a charging coil assembly can comprise a Universal Serial Bus (USP) connector coupleable to a USB port on the mobile device 100 or external controller 50. However, such USB ports and connectors come in different sizes and shapes, making general use of such USB-style charging coil assemblies difficult. Moreover, and as discussed in the above-referenced '050 Application, special provisions must be made to ensure that the charging coil assembly can communicate with and be controlled by the mobile device 100 or dedicated external controller 50. This is true because USB communications occur with a particular protocol in which communicating devices exist in a master/ slave relationship. The USB ports provided on general-purpose mobile devices 100 for example are typically configured as a slave, and thus the charging coil assembly must include USB interface circuitry programmed to act as the master. This complicates design of the charging coil assembly.

BRIEF DESCRIPTION OF THE DRAWINGS

FIG. 1 shows an Implantable Medical Device (IMD) in accordance with the prior art.

FIG. 2 shows a cross section of an IMD having a telemetry antenna and a charging coil, in accordance with the prior art.

FIG. 3 show a dedicated external controller for communicating with an IMD, in accordance with the prior art.

FIG. 4A shows a general-purpose mobile device, and FIG. 4B shows a graphical user interface of a Medical Device Application (MDA) on the mobile device for communicating with an IMD, in accordance with the prior art.

FIG. 6A shows a charging coil assembly for a mobile device to allow for charging of an IMD, in which the assembly connects to an audio port of the mobile device, and FIG. 6B shows the assembly in cross section and in relation to the IMD being charged, in accordance with an example of the invention.

FIGS. 9A-9C show other examples of the charging coil assembly, in accordance with the invention.

DETAILED DESCRIPTION

Disclosed is an improved charging coil assembly for a mobile device such as a mobile phone able to wirelessly provide power to charge a battery in an Implantable Medical Device (IMD). The assembly includes a coaxial audio connector that can be inserted into a coaxial audio port on the mobile device to allow bi-directional communications between the assembly and the mobile device. One or more housings coupled to the connector by a cable can include control circuitry, a charging coil, and a battery. The charging coil can be driven by control circuitry in the assembly, or can be driven by a charging audio signal at an audio frequency provided by the mobile device via the audio port and connector. A Charging Application on the mobile device can be used to detect and authenticate the charging coil assembly, and to render a graphical user interface on the mobile device to allow a patient to control and/or monitor charging of his IMD.

Figure 5A:
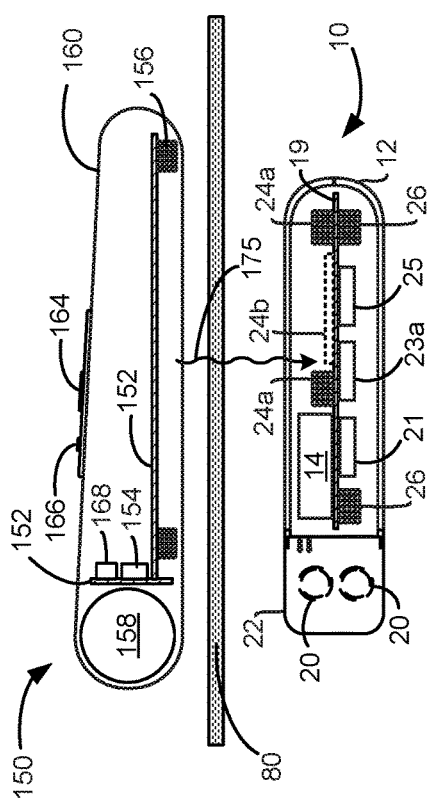
FIG. 5A shows an external charger for recharging a battery in an IMD.
Figure 5B:
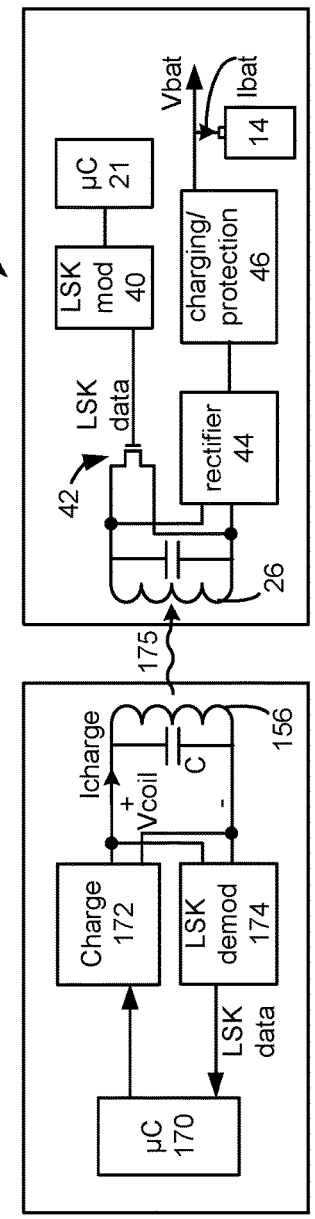
FIG. 5B shows relevant circuitry in both the external charger and the IMD, in accordance with the prior art.

A first example of the disclosed charging coil assembly 200 is shown in FIGS. 6A and 6B in perspective and cross-sectional views respectively. As shown, the assembly 200 comprises a housing 202 formed of hard plastic for example. A printed circuit board (PCB) 220 (FIG. 6B), which may be secured inside the housing 202 in a variety of well-known ways, is provided to integrate various circuitry 222 in the assembly 200, which circuitry is discussed subsequently. Also located in housing 202 and coupled to the circuitry 222 are a battery 224 and a charging coil 226, which may be used similarly to the battery 158 and charging coil 156 of the external charger 150 of the prior art (FIG. 5A) to provide a magnetic field 175 for charging the battery 14 in the IMD 10. A removable battery cover 204 may provide access to the battery 224 allowing it to be replaced if it is a primary battery. If battery 224 is rechargeable, a battery cover 204 may not be necessary, and instead battery 224 may be recharged by providing power at port 206 (e.g., a USB port) on the housing 202. The battery 224 provides the power for generation of the magnetic charging field 175 by the charging coil 226 as well as to power the circuitry 222, as explained further below.

Temperature measuring circuitry, such as one or more thermistors 227 can also be provided for measuring the temperature of the charging coil assembly 200 so that such temperature data can be sent to the mobile device 100. As is known, the magnetic charging field 175 can generate heat in the form of Eddy currents for example, which if excessive can aggravate or burn the patient. Reporting such temperature data back to the mobile device 100 allows the mobile device to control charging in light of a safe temperature set point (e.g., 41 degrees C. See, e.g., U.S. Pat. No. 8,321,029.

A cable 208 couples the electronics in the housing 202 to a coaxial connector 210, which connects to an audio port 112 on the mobile device 100. Audio port 112 may otherwise normally be connectable to a pair of headphones, a microphone, or a device having both of these functions. The connector 210 may comprise, for example, a 3.5 mm four-conductor TRRS (Tip Ring Ring Sleeve) connector for carrying a left audio output signal (L), a right audio output signal (R), an audio input signal (MIC), and a ground, as explained subsequently. Use of an coaxial audio connector 210 with the charging coil assembly 200 is preferred because mobile devices 100 almost universally have audio ports 112 of this type, regardless of the mobile device manufacturer or the operating system of the device. Use of a coaxial audio connector 210 also allows the mobile device 100 to provide power to and to bi-directionally communicate data with the assembly 200, as discussed in detail below. Note also that the mobile device 100 may include a USB port 114 for other purposes, such as to recharge the mobile device's battery (not shown).

Notice that the charging coil assembly 200 can completely lack a user interface. That being said, additional user interface elements (e.g., audio or visual indicators, switches) could be provided with the assembly 200 as well. For example, the housing 202 may include one or more user interface elements to indicate when the charging coil 226 is energized and producing a magnetic field 175; to indicate whether alignment between the charging coil 202 and IMD 10 is poor; to indicate the status of the battery 224, etc. As optionally shown in FIG. 6A, the housing 202 of the charging coil assembly 200 may additionally include a switch 205 to turn the magnetic charging field 175 on and off, although as discussed further below, the magnetic charging field is preferably turned on and off using the user interface of the mobile device 100.

Charging coil assembly 200 is beneficial in that it allows the mobile device 100 to be held in a comfortable position (such as in front of the patient), with the housing 202 and its charging coil 226 positioned distantly and proximately to the IMD 10 (such as behind the patient in an SCS application). Because the charging coil assembly 200 comprises a minimal amount of hardware, it can be relatively small, light, and low cost while still leveraging the advanced hardware and graphical user interface aspects of the mobile device 100.

Figure 7:
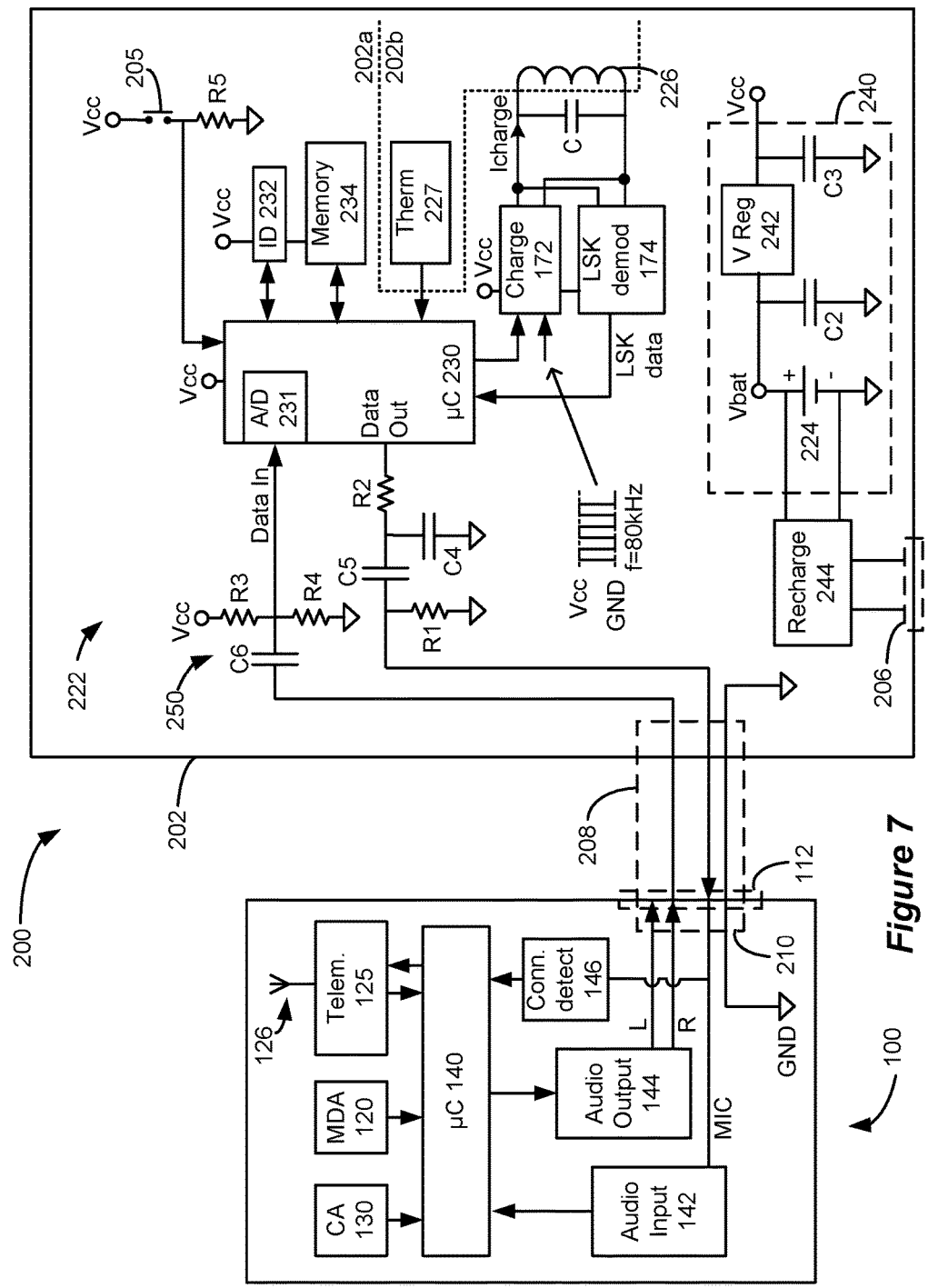
FIGS. 7 and 8 show examples of relevant circuitry in the charging coil assembly and the mobile device, in accordance with the invention.

FIG. 7 shows an example of the circuitry 222 in the charging coil assembly 200 and circuitry and modules in the mobile device 100 implicated by the assembly 200. The mobile device 100 includes control circuitry such as a microcontroller 140, which controls the main functionality of the mobile device 100. The microcontroller 140 has access to and can execute a number of different applications installed on the device, including the MDA 120 described earlier, and a Charging Application (CA) 130. Such applications comprise executable instructions written in accordance with the operating system running on the mobile device, and are stored in a non-transitory medium such as on a disk or in solid state memory. CA 130 is discussed in further detail below, and may alternatively comprise a portion of the MDA 120.

The mobile device 100 includes communication means—telemetry antenna 126 and telemetry circuitry 125—for allowing short range data communications with other devices, such as the IMD 10 when the MDA 120 is executed, as explained earlier.

The mobile device 100 also includes an audio input module 142, which is configured to receive an audio input (e.g., from a microphone; MIC) from the audio port 112, and an audio output module 144 to provide left and right audio outputs (L and R) to the audio port 112. A connector detection module 146 is used to detect when a connector (such as 210) has been inserted into the audio port 112.

The assembly circuitry 222 includes control circuitry such as a microcontroller 230. The microcontroller 230 may also have access to an assembly Identification Code (ID) 232, explained further below, and a non-volatile memory 234. (232 and 234 may also comprise a portion of the memory of the microcontroller 230). Thermistor(s) 227 report temperature data to the microcontroller 230, which can in turn report such data to the mobile device 100 via the Data Out path described further below. Optional switch 205 is also shown, which when pressed defeats pull down resistor R5 to provide a high logic (Vcc='1') input to the microcontroller 230.

Power is supplied to the circuitry 222 in the assembly 200 via a power supply voltage Vcc, which is in turn produced by power supply circuitry 240 in the assembly 200, which circuitry 240 can vary. In the example shown, power supply circuitry 240 includes the assembly battery 224, such as a 3V CR1220 Lithium button cell battery. If necessary, a voltage regulator 242 (e.g., a low drop out regulator) can be used to regulate the battery voltage Vbat to the power supply voltage Vcc needed for the assembly's circuitry 222. Such power supply regulation is not strictly necessary, and the circuitry 222 can be driven directly by Vbat as well. Capacitors C2 and C3 can be used to smooth Vbat and Vcc respectively. Recharging circuitry 244 can be used to recharge battery 224 at USB port 206 if battery 224 is rechargeable. Alternatively, battery 224 may be recharged by the mobile device 100 by an audio power signal (e.g., of 4 kHz) received from the otherwise unused audio output L, as explained in the above-incorporated '402 Publication.

The microcontroller 230 can communicate data bi-directionally with the mobile device 100 using audio signals supported by the connector 210 and the audio port 112. The microcontroller 230 can receive data from the mobile device 100 via a Data In path using the audio output(s) L and/or R (only R is used in FIG. 7), and can transmit data to the mobile device 100 via a Data Out path using the audio input MIC. In accordance with the nature of these audio channels, such data transmissions are analog in nature, and can be formatted in a variety of manners, for example, using amplitude modulation, frequency modulation, or phase encoding schemes such as Manchester encoding (not shown). In accordance with the format chosen, the audio output module 144 can be configured to modulate data from the microcontroller 140 that is to be sent to the assembly 200 through the connector 210. Likewise, the audio input module 142 can be configured to demodulate data received from the assembly 200 through the connector 210 for interpretation by the microcontroller 140. Modulation and demodulation aspects can additionally be programmed into the microcontroller 140 itself, with the audio input 142 and output 144 modules essentially acting as A/D and D/A converters.

Signal processing circuitry 250 in the assembly 200 assists in converting received analog audio signals from the connector 210 into a format interpretable by the assembly's microcontroller 230, and in converting digital data from the microcontroller 230 into analog audio signals suitable for transmission through the connector 210. Analog signals received from audio output R via the Data In path are AC-coupled to an input of microcontroller 230 via capacitor C6, with a voltage divider comprising resistors R3 and R4 used to adjust the DC offset of the signal (e.g., to Vcc/2 when R3=R4). Once the analog signal is so processed, it is preferably digitized for interpretation by the microcontroller 230, which may comprise use of an analog-to-digital (A/D) converter 231, which may be part of or separate from the microcontroller 230.

When transmitting data to the mobile device 100 via the Data Out path, resistor R2 and capacitor C4 smooth the digital output from the microcontroller 230 into a signal that is more analog in nature, which signal is then AC-coupled to the MIC audio input via capacitor C5. Resistor R1 in the assembly 200 is provided for the benefit of the connection detector 146 in the mobile device 100, which will recognize the insertion of the connector 210 into the audio port 112 upon sensing this resistance. Data transmitted from the charging coil assembly 200 to the mobile device 100 can include temperature data from the thermistor(s) 227; assembly Identification Code (ID) data 232, which the mobile device can use to authenticate the assembly 200 explained further below; any LSK data received from the IMD 10; and charging coil-IMD alignment data. Pairing of the assembly 200 to the mobile device 100 can also occur as disclosed in the '402 Publication.

Microcontroller 230 can be programmed to demodulate received data and to modulate data to be transmitted in accordance with the communication format chosen. With suitable programming, different communication formats and different modulation and demodulation schemes could be used for communications in different directions (audio output R; audio input MIC) through the connector 204.

The mobile device 100 and charging coil assembly 200 can operate to provide the magnetic charging field 175 for recharging the IMD 10's battery 14 as follows. The CA 130 detects when the connector 210 of the assembly 200 is inserted into the audio port 112 of the mobile device 100 using the mobile device's connector detection circuitry 146. The CA 130 may call for (via Data In) or automatically be provided (via Data Out) the identification code 232 of the assembly 200 to authenticate it as such, and to differentiate it from other devices such as headphones that might be inserted into the audio port 112. After optional authentication, the CA 130 may then automatically generate a charging Graphical User Interface (GUI) on the mobile device 100 to control and/or monitor charging as explained further below. Execution of the CA 130 can also be provided as a selectable option on the mobile device's home screen (FIG. 4A, similar to MDA 120), or may comprise an option within the MDA 120 itself, with the MDA 120 authenticating and automatically executing the CA 130. Execution of the CA 130 may also begin upon selection of the optional switch 205.

Note that CA 130 preferably runs in the background when installed on the mobile device 100 at least to perform charging coil assembly 200 detection and authentication and/or to detect selection of the switch 205 prior to generation of the charging GUI. CA 130 may also perform certain housekeeping, safety, and reliability tasks prior to charging GUI generation, such as closing other apps that may be running in the mobile device 100; unlocking the display 102; and disconnecting any wireless communication links to disconnect devices and systems connected to the mobile device's short-range RF antenna 126 for example.

A charging GUI rendered by the CA 130 on the display 102 of the mobile device is shown in FIG. 6A. As shown, the charging GUI can include selectable options to turn the magnetic charging field 175 on or off, such as touchable buttons if the display 102 is a touchscreen. Buttons 104 of the mobile device 100 could be used to make selections in the charging GUI as well. When the charging session begins (e.g., the patient selects "on"), the microcontroller 140 instructs audio output circuitry 144 to pass a charging instruction to the microcontroller 230 in the assembly 200 via the R audio output. In turn, the microcontroller 230 instructs charging circuitry (amplifier) 172 in the accessory 200 to pass charging current Icharge through the charging coil 226 to produce the magnetic charging field 175. This may be accomplished by driving the charging circuitry 172 with an 80 kHz square wave matching the resonance of the charging coil 226 and its tuning capacitor C.

The microcontroller 230 can adjust the strength of Icharge, and hence the strength of the magnetic charging field 175, in any number of well-known manners, including closed loop manners in which the IMD 10 telemeters feedback indicative of the strength of the magnetic charging field 175 it is receiving and/or its temperature. Such closed loop or other data can also be provided from the microcontroller 230 to the mobile device 100 via the Data Out path, and the CA 130 can in turn assess such data and send instructions to the microcontroller 230 via the Data In path regarding how Icharge should be adjusted.

During a charging session, and as shown in FIG. 6A, the charging GUI may display and periodically update information of use to the patient and received from microcontroller 230 via the Data Out path (audio input MIC). Such information may either originate in the charging coil assembly 200 itself (such as temperature data provided by the thermistor(s) 227); may arrive at the assembly 200 via telemetry (e.g., using LSK demodulator 174, such as the voltage Vbat of the IMD's battery 14); or be processed by the CA 130 based on other received data (such as an estimate of the remaining charging time). While such information is shown in FIG. 6A as text, intuitive images and icons indicative of charging information can be displayed instead. Although not shown, the assembly 200 can contain short-range RF telemetry circuitry in addition to or in place of LSK demodulator 174 to communicate data to and from the IMD 10, such as the voltage of the IMD's battery 14.

The CA 130 of the mobile device 100 may also store in the mobile device's memory charging information reported or displayed during various charging sessions to allow the patient to review charging information over a period of time. For example, charging information could be displayed graphically as a function of time, although not shown in FIG. 6A. Additionally, the advanced user interface of the mobile device 100 allows CA 130 to provide pleasant alerts to the patient, both during a charging session, and even in between charging sessions, such as by reminding the patient that his IMD 10 may need recharging.

Figure 8:
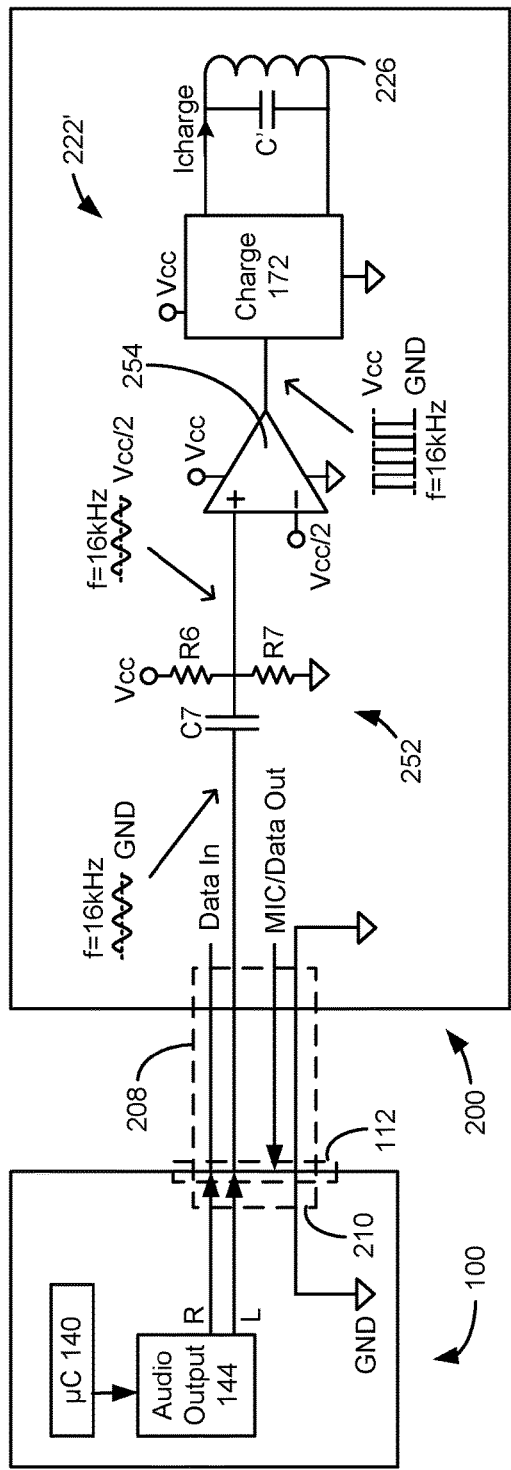

FIG. 8 shows alternative circuitry 222' for driving the charging coil 226 in the assembly 200. In this example, the charging coil 226 is driven using a charging audio signal provided from the audio output circuitry 144 in the mobile device 100 under control of CA 130, which charging audio signal is provided for example on audio output L (unused in FIG. 7). Much of the circuitry 222' in FIG. 8 can comprise the same circuitry 222 shown in FIG. 7, which is not shown again for simplicity.

In this example, the frequency of the charging audio signal is consistent with audio frequencies normally handled by the audio output circuitry 144 and the audio port 112 (e.g., between 20 Hz and 20 kHz as is generally consistent with the range of human hearing) while still being sufficient for wireless charging. For example, the charging audio signal can comprise 16 kHz. Lower frequencies (e.g., below 5 kHz) may not be sufficient for wireless charging, and so the charging audio signal more generally can fall within a preferred range of 5 kHz to 20 kHz. The charging audio signal is preferably as high a magnitude as the audio output circuitry 144 can produce, which eases the need for signal amplification in the charging coil assembly 200. Charging audio signal is preferably not modulated with data, as shown in FIG. 8, but this is not strictly necessary.

The charging audio signal provided at audio port 112/connector 210 is normally centered around ground, and so signal processing circuitry 252 (C7, R6, R7) centers the DC offset of the signal to half the power supply voltage (Vcc/2) used in the charging coil assembly 200. Thereafter, a comparator 254 referenced to Vcc/2 converts the charging audio signal to a digital square wave signal of the same frequency (e.g., 16 kHz). This digital signal then drives the charging circuitry (amplifier) 172, thus producing a charging current (Icharge) through the charging coil 226 and a magnetic charging field 175 of the same frequency (again, 16 kHz). Note that the value of the tuning capacitor C' associated with the charging coil 226 would be adjusted to a value that would resonate at this frequency when combined with the inductance of the charging coil 226. The charging coil 26 in the IMD would also preferably be tuned to this frequency to maximize energy transfer from the charging coil 226.

Figure 9A:
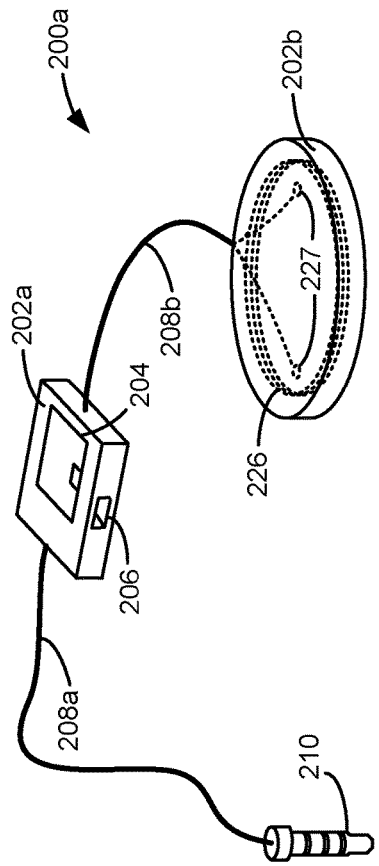

FIG. 9A shows an alternative charging coil assembly 200a in which the electronics and the charging coil 226 are separated. Specifically two housing 202a and 202b are provided, with housing 202b containing the charging coil 226 (and optionally the thermistor(s) 227), and with housing 202a containing other circuitry such as the microcontroller 230, the signal processing circuitry 250, and the power supply circuitry 240. Such separation also separates the cable, with cable portion 208b appearing between the two housings 202a and 202b, and cable portion 208a appearing between housing 202a and the connector. FIG. 7 illustrates the electrical division between the circuitry in the two housings 202a and 202b via a dotted line. Circuitry housing 202a may include the battery cover 204 and charging port 206 referred to earlier. Coil housing 202b may be formed of a more-comfortable deformable material such as silicone in this example.

The charging coil assembly 200a of FIG. 9A is beneficial because it removes assembly electronics from the area extent of the charging coil 226, which electronics can otherwise potentially interfere with the magnetic charging field 175 produced. Other examples of charging coil assemblies providing this same benefit are shown in FIGS. 9B and 9C. In assembly 200b of FIG. 9B, the battery 224 is in the same housing 202 as the charging coil 226, but moved to the side of the coil. In this regard, a larger PCB 220 is provided for supporting and electrically coupling the battery 224, the assembly circuitry 222 or 222', and the charging coil 226. Housing 202 may include a hole 225 in the center of the charging coil 116. Although not shown, the housing 202 may again include a battery cover (like 204, FIG. 6A) to permit access to the battery 224. Port 206 may again be provided to allow for recharging of the battery 224 in the assembly 200a.

The charging coil assembly 200c of FIG. 9C incorporates the battery 224 and electronics 222 or 222' in a different housing 202a than the housing 202b for the charging coil 222 (and thermistor(s); not shown), similar to assembly 220a of FIG. 9A. However, the housings 202a and 202b can connect via a port 260a and connector 260b instead of by a flexible cable (compare 208b in FIG. 9A). The port 260a and connector 260b allow the housings 202a and 202b to click together for mechanical robustness, such that such housings will touch to form an integrated battery/coil structure. However, this is not strictly necessary, and instead a cable can be used to couple 260a and 260b. Note that 260a could alternatively comprise a connector, and 260b a port. Again, housing 202a may include a battery cover for permitting access to the battery 224. Port 260a may be used to recharge the battery 224.

Although the examples of charging coil assemblies are disclosed as being useful to charging a battery in an IMD, note that they can also be used with IMDs that lack batteries, and which therefore require continuous or semi-continuous external wireless power such as provided by magnetic charging field 175 to operate.

Microcontroller control circuitry operable in the IMD 10 or in mobile device 110 can comprise for example Part Number MSP430, manufactured by Texas Instruments, which is described in data sheets at http://www.ti.com/lsds/ti/microcontroller/16-bit_msp430/overview.page?DCMP=MCU_other&HQS=msp430, which is incorporated herein by reference. However, other types of control circuitry may be used in lieu of a microcontroller as well, such as microprocessors, FPGAs, DSPs, or combinations of these, etc.

Although particular embodiments have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. An assembly coupleable to a mobile device to enable power delivery to a medical device, comprising:
   a housing;
   a charging coil within the housing;
   a battery within the housing, wherein the battery is configured to provide power to produce a magnetic charging field for the medical device from the charging coil; and
   a connector, wherein the connector is configured for connection to an audio port on a mobile device,
   wherein the charging coil is configured to be controlled by an audio signal received from the mobile device via the connector to produce the magnetic charging field.

2. The assembly of claim 1, wherein the charging coil is configured to receive a charging audio signal as the audio signal from the mobile device via the connector, and wherein the charging audio signal drives the charging coil to produce the magnetic charging field.

3. The assembly of claim 2, wherein a frequency of the charging audio signal is in the range of 5 kHz to 20 kHz.

4. The assembly of claim 2, further comprising a comparator, wherein the comparator converts the charging audio signal to a digital signal, and wherein the digital signal drives the charging coil to produce the magnetic charging field.

5. The assembly of claim 4, further comprising signal processing circuitry to center a DC offset of the charging audio signal to half a power supply voltage prior to presentation of the charging audio signal to the comparator.

6. The assembly of claim 4, further comprising an amplifier for receiving the digital signal, wherein the amplifier drives the charging coil.

7. The assembly of claim 1, further comprising control circuitry within the housing.

8. The assembly of claim 7, wherein the control circuitry is configured to receive a charging instruction as the audio signal from the mobile device via the connector, and wherein the control circuitry drives the charging coil in response to the charging instruction to produce the magnetic charging field.

9. The assembly of claim 7, wherein the control circuitry is configured to transmit data via the connector to the mobile device via an audio input channel of the connector.

10. The assembly of claim 9, wherein the data comprises one or more of a temperature of the charging coil assembly, a voltage of a battery in the medical device, and data regarding alignment between the charging coil and the medical device.

11. The assembly of claim 1, wherein the battery is not within an area extent of the charging coil.

12. The assembly of claim 1, further comprising a cable, wherein the housing is coupled to the connector by the cable.

13. The assembly of claim 1, further comprising a switch on the housing for turning the magnetic charging field on and off.

14. The assembly of claim 1, wherein the connector comprises a coaxial audio connector.

15. A system, comprising:
   a non-transitory machine-readable medium upon which are stored instructions for a charging application executable by a mobile device, wherein the charging application when executed on the mobile device is configured to:
      provide a Graphical User Interface (GUI) on the mobile device to control or monitor, or control and monitor, charging of a medical device; and
   a charging coil assembly, comprising:
      a housing;
      a charging coil within the housing;
      a battery within the housing, wherein the battery is configured to provide power to produce a magnetic charging field for the medical device from the charging coil; and
      a connector, wherein the connector is configured for connection to an audio port on the mobile device,
      wherein the charging coil is configured to be controlled by the GUI via an audio signal received from the connector to produce the magnetic charging field.

16. The system of claim 15, wherein the charging application is further configured to detect when the connector has been connected to the audio port of the mobile device, and to automatically provide the GUI on the mobile device upon detection of the connector.

17. The system of claim 15, wherein the charging application is further configured to authenticate the charging coil assembly prior to providing the GUI on the mobile device.

18. The system of claim 15, wherein the GUI provides at least one selectable option to turn the magnetic charging field on or off.

19. The system of claim 15, wherein the charging application is further configured to receive data from the charging coil assembly during production of the magnetic charging field.

20. The system of claim 15, wherein the charging application is further configured to cause the mobile device to produce a charging audio signal as the audio signal, wherein the charging coil assembly is configured to receive the charging audio signal from the mobile device via the connector, and wherein the charging audio signal drives the charging coil to produce the magnetic charging field.

21. The system of claim 20, wherein a frequency of the charging audio signal is in the range of 5 kHz to 20 kHz.

22. The system of claim 15, wherein the charging coil assembly further comprises control circuitry within the housing, wherein the charging application is further configured to produce a charging instruction as the audio signal, wherein the control circuitry is configured to receive the charging instruction from the mobile device via the connector, and wherein the control circuitry drives the charging coil in response to the charging instruction to produce the magnetic charging field.

23. The system of claim 22, wherein the control circuitry is configured to transmit data via the connector to the mobile device via an audio input channel of the connector.

24. The system of claim 15, further comprising a cable, wherein the housing is coupled to the connector by the cable.

25. The system of claim 15, wherein the connector comprises a coaxial audio connector.

* * * * *